United States Patent [19] [11] 4,285,919
Klotz et al. [45] Aug. 25, 1981

[54] METHOD OF PREPARING A METAL-CATION-DEFICIENT CRYSTALLINE BOROSILICATE

[75] Inventors: Marvin R. Klotz, Batavia; Stephen R. Ely, West Chicago, both of Ill.

[73] Assignee: Standard Oil Company (Indiana), Chicago, Ill.

[21] Appl. No.: 973,178

[22] Filed: Dec. 26, 1978

[51] Int. Cl.$^3$ ............................................. C01B 35/10
[52] U.S. Cl. .................................... 423/277; 252/432
[58] Field of Search .................. 423/277, 326–330, 423/335; 252/431 N, 432, 455 Z; 260/448.2 N

[56] References Cited

U.S. PATENT DOCUMENTS

| 3,306,922 | 2/1967 | Barrer et al. ..................... 260/448 C |
| 3,308,069 | 3/1967 | Wadlinger et al. ............... 423/328 X |
| 3,328,119 | 6/1967 | Robson ................................. 423/277 |
| 3,702,886 | 11/1972 | Argauer et al. ...................... 423/328 |
| 3,941,871 | 3/1976 | Dwyer et al. ........................ 423/326 |
| 4,060,590 | 11/1977 | Whittam et al. ..................... 423/328 |
| 4,061,724 | 12/1977 | Grose et al. ..................... 423/335 X |
| 4,071,377 | 1/1978 | Schwuger et al. ................ 423/329X |

FOREIGN PATENT DOCUMENTS 984502 2/1965 United Kingdom ..................... 423/329

*Primary Examiner*—Edward J. Meros
*Attorney, Agent, or Firm*—James L. Wilson; William T. McClain; William H. Magidson

[57] ABSTRACT

There is disclosed a method for preparing a metal-cation-deficient crystalline borosilicate, which method comprises: (1) preparing a mixture containing an oxide of silicon that is substantially free of metal cations, an oxide of boron, ammonium hydroxide, alkylammonium cation or a precursor of an alkylammonium cation, and water; and (2) maintaining the mixture at suitable reaction conditions to effect formation of the borosilicate.

There are also disclosed the crystalline borosilicate that results from the above-described method of preparation and uses of that borosilicate.

10 Claims, No Drawings

4,285,919

METHOD OF PREPARING A METAL-CATION-DEFICIENT CRYSTALLINE BOROSILICATE

BACKGROUND OF THE INVENTION

This invention relates to novel crystalline borosilicates, their method of preparation, and their use. More particularly, this invention relates to metal-cation-deficient crystalline borosilicate molecular sieve materials having catalytic properties and to various uses of such crystalline borosilicates.

Both natural and synthetic zeolitic materials have been known to have catalytic capabilities for many hydrocarbon conversion processes. Such zeolitic materials, often referred to as molecular sieves, are ordered porous crystalline aluminosilicates having a definite structure with large and small cavities interconnected by channels. The cavities and channels that are present throughout the crystalline material are generally uniform in size and permit selective separation of hydrocarbons. Consequently, these materials in many instances have come to be classified in the art as molecular sieves and are utilized for certain catalytic properties, as well as for selective adsorptive properties. The catalytic properties of these zeolitic materials are affected also, at least to some extent, by the size of the molecules that are allowed to penetrate selectively the crystal structure. Presumably, these molecules which penetrate the crystal structure of the crystalline molecular sieve material are contacted with active catalytic sites within the ordered structure of the material.

Generally, the term "molecular sieve" includes a wide variety of positive-ion-containing crystalline materials, which may be either natural or synthetic. They are generally characterized as crystalline aluminosilicate material, although other crystalline materials may be included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalences of the $AlO_4$ tetrahedra are balanced by the use of positive ions, for example, alkali-metal cations or alkaline-earth-metal cations.

Many synthetic crystalline materials have been developed. Crystalline aluminosilicates are among such crystalline materials and, as described in the patent literature and the published journals, are designated by letters or other convenient symbols. Typical examples of such crystalline aluminosilicates are Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), and others.

U.S. Pat. No. 3,702,886, which discloses Zeolite ZSM-5 and its method of preparation, teaches the production of a zeolite wherein aluminum or gallium oxides are present in the crystalline structure, along with silicon or germanium oxides. The latter and the former are reacted in a specific ratio to produce a class of zeolites designated ZSM-5, which is limited to crystalline alumino- or gallo-silicates or germanates and which has a specified X-ray diffraction pattern. The above ZSM-11 and ZSM-12 patents are similarly limited to crystalline alumino- or gallo-silicates or germinates, also having specified X-ray diffraction patterns.

Manufacture of the ZSM materials utilizes a mixed base system in which sodium aluminate and silicon-containing material are mixed together with sodium hydroxide and an organic base, such as tetrapropylammonium hydroxide or tetrapropylammonium bromide, under specified reaction conditions, to form the desired crystalline aluminosilicate.

U.S. Pat. No. 3,941,871 claims and teaches an organosilicate having very little aluminum in its crystalline structure and possessing an X-ray diffraction pattern similar to the ZSM-5 composition.

Recently, as disclosed in a co-pending United States patent application, Ser. No. 897,360, filed in the United States Patent and Trademark Office on Apr. 18, 1978, there has been found a novel family of stable synthetic crystalline materials characterized as borosilicates, which are identified as AMS-1B and which have a specified X-ray diffraction pattern. Such crystalline borosilicates are formed by reacting a boron oxide and a silicon-containing material in a basic medium in the presence of an alkali metal or an alkaline earth metal.

U.S. Pat. No. 3,328,119 is directed to a synthetic crystalline aluminosilicate containing a minor amount of boria as an integral part of its crystal framework. This crystalline material is a boron-containing aluminosilicate and is not a crystalline borosilicate.

U.S. Pat. Nos. 3,329,480 and 3,329,481 relate to "zircono-silicates" and "titano-silicates", respectively.

U.S. Pat. Nos. 4,029,716; 4,049,573; 4,067,920; 4,078,009; and 4,086,287 relate to crystalline aluminosilicate zeolites having a silica-to-alumina ratio of at least about 12 and a constraint index within the approximate range of 1 to 12, and having combined therewith boron in an amount of at least about 0.2 weight percent as a result of reaction of the zeolite with a boron-containing compound. This is a crystalline aluminosilicate containing some boron and is not a crystalline borosilicate.

There has also been disclosed in the prior art the preparation of high-purity crystalline aluminosilicates, which aluminosilicates are prepared by the use of alkylammonium hydroxides or ammonium hydroxides. Such synthesized nitrogenous crystalline aluminosilicates are metal-cation deficient. "Hydrothermal Chemistry of the Silicates. Part IX. Nitrogenous Aluminosilicates." R. M. Barrer and P. J. Denny, J. CHEM. SOC., 971 (1961); and "Synthesis and Crystal Structure of Tetramethylammonium Gismondine", C. Baerlocher and W. M. Meier, HELVETICA CHIMICA ACTA, 53, 1285 (1970). Such disclosures do not consider crystalline borosilicates.

There has now been derived crystalline borosilicate material that is deficient in metal cations, that is, it is substantially free of metal cations.

SUMMARY OF THE INVENTION

Broadly, according to the present invention, there is provided a method for preparing a crystalline borosilicate which is substantially free of metal cations, which method comprises: (1) preparing a mixture containing an oxide of silicon which is substantially free of metal cations, an oxide of boron, ammonium hydroxide, alkylammonium cation or a precursor of an alkylammonium cation, and water; and (2) maintaining said mixture at suitable reaction conditions to effect formation of said borosilicate, said reaction conditions comprising a reaction temperature within the range of about 25° C. (77° F.) to about 300° C. (572° F.), a pressure of at least the vapor pressure of water at the reaction temperature, and a reaction time that is sufficient to effect crystallization.

According to the present invention, there is provided also a crystalline borosilicate which is substantially free of metal cations and which comprises a molecular sieve material having the following composition in terms of mole ratios of oxides:

$$0.9\pm 0.2\ M_{2/n}O:B_2O_3:YSiO_2:ZH_2O,$$

wherein M is at least one non-metal cation having a valence of n, Y is within the range of 4 to about 600, and Z is within the range of 0 to about 160; the borosilicate being characterized by its method of preparation, which method is the method described hereinabove.

There is also provided a process for the conversion of a hydrocarbon stream, which process comprises contacting said hydrocarbon stream at conversion conditions with the crystalline borosilicate described hereinabove.

More particularly, there is disclosed a process for the isomerization of a xylene-containing feed, which process comprises contacting said feed at isomerization conditions with a catalyst comprising the crystalline borosilicate described hereinabove.

The crystalline borosilicates of the present invention can be employed in various processes, some of which are reforming, cracking, hydrocracking, transalkylation, disproportionation, isomerization, and alkylation. They are particularly suitable for the isomerization of xylenes and the conversion of ethylbenzene and they can be used to convert alcohols, such as methanol, to useful products, such as aromatics or olefins.

DESCRIPTION AND SPECIFIC EMBODIMENTS

The present invention relates to a novel synthetic crystalline molecular sieve material, a crystalline borosilicate.

The family of such crystalline borosilicate materials, which are identified as AMS-1B borosilicates, has a particular X-ray powder diffraction pattern as is shown in the various tables hereinafter. Such a crystalline borosilicate can generally be characterized, in terms of the mole ratios of oxides, as follows in Expression I:

$$0.9\pm 0.2\ M_{2/n}O:B_2O_3:YSiO_2:ZH_2O \quad (I)$$

wherein M is at least one cation, n is the valence of the cation, Y is within the range of 4 to about 600, and Z is within the range of 0 to about 160. or more.

In another instance, a crystalline borosilicate can be represented in terms of mole ratios of oxides for the crystalline material not yet activated or calcined at high temperatures as follows in Expression II:

$$0.9\pm 0.2\ (WR_2O+[1-W]\\ M_{2/n}O):B_2O_3:YSiO_2:ZH_2O \quad (II)$$

wherein R is an alkylammonium cation, M is at least one cation, n is the valence of the cation M, Y is a value within the range of 4 to about 600, Z is a value within the range of 0 to about 160, and W is a value greater than 0 and less than 1.

In Expression I, M can represent an alkali-metal cation, an alkaline-earth-metal cation, an ammonium cation, an alkylammonium cation, a hydrogen cation, a catalytically-active-metal cation, or mixtures thereof. In Expression II, M can represent an alkali-metal cation, an alkaline-earth-metal cation, an ammonium cation, an alkylammonium cation, a hydrogen cation, a catalytically-active metal cation, or mixtures thereof.

Advantageously, the value for Y falls within the range of 4 to about 500. Suitably, Y is within the range of 4 to about 300; preferably, within the range of about 50 to about 160; and more preferably, within the range of about 80 to about 120.

Suitably, Z is within the range of 0 to about 40.

The original cation "M" in the above expressions can be replaced, at least in part, in accordance with techniques well known in the art by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate catalytically active especially for hydrocarbon conversion. These materials include hydrogen, rare earth metals, aluminum, metals of Groups IB, IIB and VIII of the Periodic Table of Elements, noble metals, manganese, chromium, and other catalytically active materials and metals known to the art. The catalytically active components can be present in an amount from about 0.05 to about 25 weight percent of the AMS-1B crystalline borosilicate. The Periodic Table of Elements referred to hereinabove is that found on page 628 of WEBSTER'S SEVENTH NEW COLLEGIATE DICTIONARY, G. & C. Merriam Company, Springfield, Massachusetts, U.S.A. (1963).

If any alkali metal or alkaline-earth metal were present in the crystalline borosilicate material, it could be replaced with an appropriate metal cation by means of well-known cation-exchange techniques. Such cation-exchange would in all probability improve the catalytic activity of the particular crystalline borosilicate.

Now, removal of an alkali-metal cation or alkaline-earth-metal cation is no longer necessary. A method for the preparation of a crystalline borosilicate that is substantially free of metal cations has been developed. The term "substantially free of metal cations" is used herein to mean that there is less than 0.1 mole of $M_{2/n}O$ per mole of $B_2O_3$ in the expression representing the composition of the borosilicate, wherein "M" represents a metal cation and "n" is the valence of the metal cation. Such borosilicate, its method of preparation, and its uses constitute the present invention.

Members of the family of AMS-1B crystalline borosilicates possess a specified and distinguishing X-ray powder diffraction pattern, which can be obtained by means of X-ray powder diffraction measurements.

For the X-ray powder diffraction measurements made during the work discussed hereinafter, the X-ray diffractometer was a Phillips instrument which utilized copper K alpha radiation in conjunction with an AMR focusing monochromometer and a theta compensating slit, in which its aperture varies with the theta angle. The output from the diffractometer was processed through a Canberra hardware/software package and reported by way of a strip chart and tabular printout. The compensating slit and the Canberra package tend to increase the peak-to-background ratios while reducing the peak intensities at low theta angles [large interplanar spacings] and increasing the peak intensities at high theta angles [small interplanar spacings].

In order to facilitate the reporting of the results obtained, the relative intensities i.e., relative peak heights, were arbitrarily assigned the following values:

| Relative Peak Height | Assigned Strength |
|---|---|
| less than 10 | VW (very weak) |
| 10–19 | W (weak) |
| 20–39 | M (Medium) |
| 40–70 | MS (medium strong) |
| greater than 70 | VS (very strong) |

These assigned strengths are used hereinafter.

In the subsequent tables, interplanar spacings are represented by "d" and are expressed in terms of Angstrom units (Å) or nanometers (nm). The relative intensities are represented by the term "I/Io" and the term "assigned strength" is represented by "A.S.".

The AMS-1B crystalline borosilicate of the present invention provides an X-ray diffraction pattern comprising the following X-ray diffraction lines and assigned strengths.

| d, Å | d, nm | A.S. |
|---|---|---|
| 11.2 ± 0.2 | 1.12 ± 0.02 | W–VS |
| 10.0 ± 0.2 | 1.00 ± 0.02 | W–MS |
| 5.97 ± 0.07 | 0.597 ± 0.007 | W–M |
| 3.82 ± 0.05 | 0.382 ± 0.005 | VS |
| 3.70 ± 0.05 | 0.370 ± 0.005 | MS |
| 3.62 ± 0.05 | 0.362 ± 0.005 | M–MS |
| 2.97 ± 0.02 | 0.297 ± 0.002 | W–M |
| 1.99 ± 0.02 | 0.199 ± 0.002 | VW–M |

Such X-ray diffraction pattern has been reported for AMS-1B crystalline borosilicates in co-pending application United States Ser. No. 897,360, which was filed on Apr. 18, 1978.

Broadly, according to the present invention, there is provided a method for preparing a metal-cation-deficient borosilicate, which method comprises: (1) preparing a mixture containing an oxide of silicon that is substantially free of metal cations, an oxide of boron, ammonium hydroxide, alkylammonium cation or a precursor of an alkylammonium cation, and water; and (2) maintaining said mixture at suitable reaction conditions to effect formation of said borosilicate, said reaction conditions comprising a reaction temperature within the range of about 25° C. (77° F.) to about 300° C. (572° F.), a pressure of at least the vapor pressure of water at the reaction temperature, and a reaction time that is sufficient to effect crystallization. Of course, such metal-cation-deficient borosilicate is substantially free of metal cations, e.g., alkali-metal cations and alkaline-earth-metal cations. Therefore, the metal-cation-deficient borosilicate is a borosilicate that contains less than 0.1 mole of $M_{2/n}O$ per mole of $B_2O_3$ in the expression representing the composition of the borosilicate, wherein "M" represents a metal cation and "n" is the valence of the metal cation.

It is to be understood that the expression "metal-cation-deficient borosilicate" or the expression "borosilicate which is substantially free of metal cations" refers to the borosilicate material prior to the incorporation of a catalytically active metal therein by cation exchange. Please note that the metal-cation-deficient borosilicate or borosilicate which is substantially free of metal cations of the present invention is prepared without employing a cation-exchange in order to achieve the metal-cation deficiency.

In addition, there is provided a crystalline borosilicate which is substantially free of metal cations and which comprises a molecular sieve material having the following composition in terms of mole ratios of oxides:

$$0.9 \pm 0.2\ M_{2/n}O:B_2O_3:YSiO_2:ZH_2O,$$

wherein M is at least one non-metal cation having a valence of n, Y is within the range of 4 to about 600, and Z is within the range of 0 to about 160; said borosilicate being characterized by its method of preparation, which method comprises: (1) preparing a mixture containing an oxide of silicon that is substantially free of metal cations, an oxide of boron, ammonium hydroxide, alkylammonium cation or a precursor of an alkylammonium cation, and water; and (2) maintaining said mixture at suitable reaction conditions to effect formation of said borosilicate, said reaction conditions comprising a reaction temperature within the range of about 25° C. (77° F.) to about 300° C. (572° F.), a pressure of at least the vapor pressure of water at the reaction temperature, and a reaction time that is sufficient to effect crystallization. The metal cations of which the borosilicate is substantially free include, but are not limited to, alkali-metal cations and alkaline-earth-metal cations.

For the composition equation representing the crystalline borosilicate of the present invention, the value of Y advantageously falls within the range of 4 to about 500, suitably within the range of 4 to about 300, and preferably within the range of about 50 to about 160. Moreover, the value of Z suitably is within the range of 0 to about 40.

The AMS-1B crystalline borosilicate of the present invention can be prepared generally by mixing an aqueous medium of oxides of boron and silicon, together with alkylammonium cations or a precursor of alkylammonium cations, such as an alkylamine, an alkylamine plus an alkyl hydroxide, an alkylamine plus an alkyl halide, or an alkylamine plus an alkyl acetate. The alkyl groups in the alkylammonium cations may be the same, or mixed, such as tetraethyl-, or diethyl-dipropyl-ammonium cations. Alkylamines, such as 1,6-hexanediamine, other diamines, or monoalkyl-, dialkyl-, or trialkylamines, can be used. The mole ratios of the various reactants can be varied considerably to produce the AMS-1B crystalline borosilicates. In particular, the mole ratios of the initial reactant concentrations for producing the borosilicate can vary as is indicated in Table I below.

Examples of oxides of boron are $H_3BO_3$, $B_2O_3$, and $H_3B_3O_6$. Examples of oxides of silicon are silicic acid, ammonium silicate, tetraalkyl silicates, and Ludox, which is a stabilized polymer of silicic acid manufactured by E. I. du Pont de Nemours & Co.

TABLE 1

| MOLE RATIOS OF INITIAL REACTANTS | | | |
|---|---|---|---|
| | BROAD | PRE-FERRED | MOST PREFERRED |
| $SiO_2/B_2O_3$ | 1–400 | 2–150 | 4–80 |
| $R_2O/[R_2O + (NH_4)_2O]$ | 0.01–1 | 0.01–1 | 0.01–1 |
| $NH_4+/[NH_4+ + M^n]$ | 0.7–1 | 0.9–1 | 0.97–1 |
| $NH_3/SiO_2$ | 0.02–20 | 0.02–8 | 0.04–5 |
| $H_2O/NH_3$ | 2–2,000 | 5–2,000 | 12–1,000 |

In Table I, R is an alkylamine, an alkylammonium cation, preferably tetra-n-propylammonium cation or tetraethylammonium cation, and M is at least one metal cation having the valence of n, such as an alkali-metal cation or an alkaline-earth-metal cation. The above quantities can be varied in concentration in the aqueous medium.

During preparation, acidic conditions generally should be avoided. However, during the initial mixing of reactants, a pH of 5.7, or lower, can be used prior to the addition of ammonium hydroxide. Advantageously, the pH of the mixture in the reaction system prior to crystallization should fall within the range of about 8.2 to about 11.5. Preferably, the pH of the system should be about 8.4 to about 11.2. A proper pH is conducive to the incorporation of boron into the molecular sieve structure.

By simple regulation of the quantity of boron (represented as $B_2O_3$) in the reaction mixture, it is possible to vary the $SiO_2/B_2O_3$ molar ratio in the final product in a range of about 40 to about 600, or more. In instances where an effort is made to minimize aluminum in the borosilicate crystal structure, the molar ratios of $SiO_2/Al_2O_3$ can easily exceed a ratio of 2000:1 to 3000:1, or more. This ratio is generally only limited by the availability of aluminum-free raw materials.

Molar ratios of $SiO_2/B_2O_3$ in the final crystalline product can vary from 4 to about 600, or more. Actual laboratory preparations under the general conditions described herein produce $SiO_2/B_2O_3$ molar ratios starting around 60 or lower. Lower ratios might be produced using production methods which still are in the scope of the teachings of this specification.

Concentrated ammonium hydroxide is added at any stage of the mixing of the various components. However, it can be added conveniently to the solution containing the oxide of boron, oxide of silicon, the alkylammonium cation or precursor of an alkylammonium cation, and water prior to crystallization. The pH of the system should fall within the range of about 8.2 to about 11.5.

Under reasonably controlled conditions and through the use of the above information, the AMS-1B crystalline borosilicate of the present invention will be produced. The temperature is typically within the range of about 25° C. (77° F.) to about 300° C. (572° F.), or higher; advantageously within the range of about 90° C. (194° F.) to about 225° C. (437° F.); and preferably within the range of about 110° C. (230° F.) to about 200° C. (392° F.). The digestion time required for crystallization is typically within the range of about 8 hours to about 3 weeks; advantageously within the range of about 1 day to about 12 days; and preferably within the range of about 2 days to about 7 days. The value of the molar ratio of added $NH_3$/silica should be at least 0.02. Especially preferred conditions include a temperature around 165° C. (329° F.) for a period of about 2 days to about 7 days.

The material thus formed can be separated and recovered by well-known means, such as filtration. This material can be mildly dried over a period extending from a few hours to a few days at varying temperatures, e.g., 21° C. (70° F.) to 204° C. (400° F.) to form a dry cake, which itself can then be crushed to a powder or to small particles and extruded, pelletized, or made into forms suitable for its intended use. Generally, the material prepared after the mild drying conditions will contain the alkylammonium ion within the solid mass and a subsequent activation or calcination procedure is necessary, if it is desired to remove this material from the formed product.

Typically, the high temperature calcination conditions will take place at temperatures anywhere from about 260° C. (500° F.) to about 871° C. (1,600° F.), or higher. Extreme calcination temperatures may prove detrimental to the crystal structure or may totally destroy it. There is generally no need for going beyond about 593° C. (1,100° F.) in order to remove the alkylammonium cation from the original crystalline material formed.

In a typical preparation of an AMS-1B crystalline borosilicate of the present invention, a compound of boron, such as boric acid, is dissolved in water (preferably, distilled or deionized water). A tetraalkylammonium compound, such as tetra-n-propylammonium bromide, is added to the above solution. A compound of silicon substantially free of metal cations, such as a silica sol, is added rapidly to the solution, while the solution is being agitated vigorously. Vigorous agitation is continued for about 15 minutes. Concentrated ammonium hydroxide can be added at any point during the addition and mixing of the other ingredients of the solution. Preferably, the compound of silica is added last, in the case of the ingredients other than ammonium hydroxide. When all of the ingredients are in the solution, it is placed in an autoclave, or other pressurized vessel, that is maintained at a temperature of about 165° C. (329° F.). Preferably, a stirred autoclave is used. The solution is kept in the autoclave for a period of time of about 2 days to about 7 days for crystallization. It is preferred that the crystallization temperature be maintained below the decomposition temperature of the tetraalkylammonium compound. At the completion of the crystallization, the crystalline molecular sieve is removed from the autoclave, filtered, and washed with water. The molecular sieve material is dried in a forced draft oven at 110° C. (230° F.) for about 16 hours and is then heated in air in a manner such that the temperature rise does not exceed 111° C. (200° F.) per hour until a temperature of about 538° C. (1,000° F.) is reached. Calcination at this temperature is then continued for about 4 hours.

In general, the surface area of the AMS-1B crystalline borosilicate, as determined by BET surface area analysis, falls within the range of about 300 m²/gm to about 450 m²/gm and the particles of the borosilicate have a maximum diameter, as determined by a scanning electron microscope, of about 2 microns.

The AMS-1B crystalline borosilicates of the present invention are useful as catalysts for various hydrocarbon conversion processes and they are suitable for chemical adsorption. Some of the hydrocarbon conversion processes for which the borosilicates appear to have relatively useful catalytic properties are fluidized catalytic cracking; hydrocracking; the isomerization of normal paraffins, olefins, and naphthenes; the reforming of naphthas and gasoline-boiling-range feedstocks; the isomerization of aromatics, especially the isomerization of alkylaromatics, such as xylenes; the disproportionation of aromatics, such as toluene, to form mixtures of other more valuable products including benzene, xylene, and other higher methyl substituted benzenes; transalkylation; hydrotreating; alkylation; hydrodealkylation; hydrodesulfurization; and hydrodenitrogenation. They are particularly suitable for the isomerization of alkylaromatics, such as xylenes, and for the conversion of ethylbenzene. The AMS-1B borosilicates, in certain ion-exchanged forms, can be used to convert alcohols, such as methanol, to useful products, such as aromatics or olefins.

The present composition is also suitable for hydrocarbon isomerization and disproportionation. It is especially useful for liquid or vapor phase isomerization of xylenes and especially for the isomerization of mixed xylenes to para-xylene. Operating conditions for the isomerization of a xylene feed broadly comprise a temperature of about 93° C. (200° F.) to about 538° C. (1,000° F.), a hydrogen-to-hydrocarbon mole ratio of about 0 to about 20, a weight hourly space velocity (WHSV) of about 0.01 weight unit of feed per hour per weight unit of catalyst (hr$^{-1}$) to about 90 hr$^{-1}$, and a pressure of about 0 psig (101 kPa) to about 1,000 psig (6,998 kPa). Advantageously, the conditions comprise a temperature of about 204° C. (400° F.) to about 482° C. (900° F.), a hydrogen-to-hydrocarbon mole ratio of about 1 to about 12, and a WHSV of about 1 hr.$^{-1}$ to about 20 hr.$^{-1}$, and a pressure of about 10 psig (170 kPa) to about 500 psig (3,550 kPa). The preferred conditions for the isomerization of xylenes comprise a temperature of about 316° C. (600° F.) to about 454° C. (850° F.), a hydrogen-to-hydrocarbon mole ratio of about 2 to about 8, a WHSV of about 1 hr.$^{-1}$ to about 10 hr.$^{-1}$, and a pressure of about 100 psig (793 kPa) to about 300 psig (2,172 kPa).

The choice of catalytically active metals to be placed on the AMS-1B crystalline borosilicate can be selected from any of those well known in the art. Nickel or molybdenum seems to be especially appropriate for the isomerization of aromatics. When the AMS-1B crystalline borosilicate has suitable cations placed on its ion-exchangeable sites and it is used as a catalyst in isomerization processes, reasonably high selectivities for production of desired isomers are obtained.

The claimed AMS-1B crystalline borosilicates can be used also as adsorbents to selectively adsorb specific isomers or hydrocarbons in general from a liquid or vapor stream.

The ability for these materials to be stable under high temperatures or in the presence of other normal deactivating agents appears to make this class of crystalline materials relatively valuable for high-temperature operations.

The AMS-1B crystalline borosilicates of the present invention can be used as catalysts or as adsorbents, whether in their original form, the hydrogen form, or any other univalent or multivalent cationic form. Mixtures of cations may be employed. The AMS-1B crystalline borosilicates can also be used in intimate combination with a hydrogenating component, such as tungsten, vanadium, molybdenum, rhenium, nickel, cobalt, chromium, manganese, or a noble metal, such as platinum, or palladium, or rare earth metals, where a hydrogenation-dehydrogenation function is to be performed. Such components can be exchanged into the composition at the cationic sites, represented by the term "M" in the expressions presented hereinabove, impregnated therein, or physically and intimately admixed therewith. In one example, platinum can be placed on the borosilicate with a platinum-metal-containing cation.

The impregnation of a hydrogenating metal on the crystalline borosilicate or on a support comprising the crystalline borosilicate suspended in and distributed throughout a matrix of a porous refractory inorganic oxide, such as an alumina, can provide a suitable catalytic composition. For example, a catalyst comprising molybdenum impregnated on a composition of AMS-1B crystalline borosilicate suspended in an alumina matrix, when used to isomerize a feed of mixed xylenes, furnishes improved selectivity and by-product values.

Since the AMS-1B crystalline borosilicates of the present invention are originally in the hydrogen form, a catalytically active metal ion can be easily placed on the borosilicate structure by ion-exchange techniques.

The original cation associated with the AMS-1B crystalline borosilicate can be replaced, as mentioned hereinabove, by a wide variety of other cations according to techniques which are known in the art. Ion exchange techniques known in the art are disclosed in many patents, including U.S. Pat. Nos. 3,140,249, 3,140,251; and 3,140,253.

A catalytically active material can be placed onto the borosilicate structure by ion exchange, impregnation, or other suitable contact means, followed by washing (if appropriate), drying at a temperature of about 66° C. (150° F.) to about 316° F. (600° F.), and heat treating in a suitable atmosphere, such as oxygen, nitrogen, or combinations thereof, at a temperature of about 260° C. (500° F.) to about 816° C. (1,500° F.), typically about 520° C. (1,000° F.), usually for a period of time of about 0.5 hour to about 20 hours. This procedure can be repeated one or more times.

Ion-exchange of the cationic sites within the crystalline material will generally have a relatively insignificant effect on the overall X-ray diffraction pattern that the crystalline borosilicate material generates. Small variations may occur at various spacings on the X-ray pattern, but the overall pattern remains essentially the same. Small changes in the X-ray diffraction patterns may also be the result of processing differences during manufacture of the borosilicate; however, the material will still fall within the generic class of AMS-1B crystalline borosilicates defined in terms of their X-ray diffraction patterns as shown in the tables found herein, or in the examples that follow.

The crystalline borosilicate of the present invention may be incorporated as a pure borosilicate in a catalyst or adsorbent or may be admixed with various binders or bases depending upon the intended process use. In many instances, the crystalline borosilicate can be pelletized or extruded. The crystalline borosilicate can be combined with inactive materials, such as alpha-alumina; or active materials, such as gamma-alumina; synthetic or naturally-occurring zeolites, as well as inorganic or organic materials which would be useful for binding the borosilicate. Refractory inorganic oxides, such as aluminas, are suitable materials. Other well-known materials include mixtures of silica, silica-alumina, alumina clays, such as bentonite or kaolin, or other binders well known in the art. The crystalline borosilicate can also be mixed intimately with porous matrix materials, such as silica-zirconia, silica-magnesia, silica-alumina, silica-thoria, silica-beryllia, silica-titania, as well as three component compositions including, but not limited to, silica-alumina-thoria and many other materials well known in the art. The borosilicate can be blended into a sol or gel of the porous matrix material with subsequent gelling of the blend; or it, in the form of solid particles, can be physically admixed with solid particles of the matrix material. In either case, the resulting composition comprises the crystalline borosilicate suspended in and distributed throughout a matrix of the other porous material. Such composition can be pelletized or extruded. Typically, the crystalline borosilicate is suspended in and distributed throughout a matrix of a refractory inorganic oxide, such as an alumina. The crystalline borosilicate content can vary anywhere from a few up to 100 wt.% of the total finished product. Typical catalytic compositions contain about 2 wt.% to about 80 wt.% crystalline borosilicate material.

Typically, an active hydrocarbon conversion catalyst employing the above-described borosilicate can be prepared conveniently. Metallic cations, for example, nickel ions, are introduced onto the borosilicate. Typically, this introduction is carried out by exchanging the borosilicate one or more times with an aqueous solution of a compound of the metal to be exchanged therein, for example, nickelous nitrate, at a temperature of about 85° C. (185° F.) to about 100° C. (212° F.).

The metal-exchanged borosilicate, in a finely-divided form, is dispersed into a sol or gel of a high-grade-purity refractory inorganic oxide, such as gamma-alumina. With constant stirring, a solution of ammonium hydroxide is added to promote gellation. The resulting gelled mixture is then dried and calcined, as described hereinabove, pulverized to a convenient particle size, and formed into pellets or extrudate.

A suitable method for the preparation of a catalytic composition of the present invention comprises the introduction of finely-divided borosilicate material and a compound containing the catalytically active metal into a sol or gel of a suitable matrix material, such as alumina; a thorough blending of the resulting mixture; and subsequent gelling of the mixture by the addition of a suitable material, such as an ammonium hydroxide solution. The resulting gel is then dried and calcined according to methods discussed herein. In such a composition, the crystalline borosilicate and the catalytically active metal would be suspended in and distributed throughout the matrix material.

According to the present invention, there is provided a catalytic composition which comprises a crystalline borosilicate and a porous refractory inorganic oxide, said borosilicate and said inorganic oxide having been intimately admixed with one another, said borosilicate being substantially free of metal cations and comprising a molecular sieve material having the following composition in terms of mole ratios of oxides:

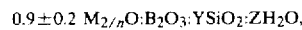

$$0.9 \pm 0.2\ M_{2/n}O:B_2O_3:YSiO_2:ZH_2O,$$

wherein M is at least one non-metal cation having a valence of n, Y is within the range of 4 to about 600, and Z is within the range of 0 to about 160; said borosilicate being characterized by its method of preparation, which method comprises: (1) preparing a mixture containing an oxide of silicon that is substantially free of metal cations, an oxide of boron, ammonium hydroxide, alkylammonium cation or a precursor of an alkylammonium cation, and water; and (2) maintaining said mixture at suitable reaction conditions to effect formation of said borosilicate, said reaction conditions comprising a reaction temperature within the range of about 25° C. (77° F.) to about 300° C. (572° F.), a pressure of at least the vapor pressure of water at the reaction temperature, and a reaction time that is sufficient to effect crystallization. Furthermore, the catalytic composition can be one wherein at least one catalytically-active metal is placed onto said calcined borosilicate before said borosilicate is mixed with the porous refractory inorganic oxide. The catalytic composition can be one wherein the inorganic oxide is an alumina. The catalytically active metal is conveniently nickel or molybdenum. Molybdenum is preferred.

There is provided, according to the present invention, a process for the conversion of a hydrocarbon stream, which process comprises contacting said stream at conversion conditions with the catalytic composition described hereinabove or the crystalline borosilicate described hereinabove. There is provided also a process for the catalytic isomerization of a xylene feed, which process comprises contacting said feed at isomerization conditions with the catalytic composition described hereinabove or the crystalline borosilicate described hereinabove. Such isomerization conditions comprise a temperature of about 93° C. (200° F.) to about 538° C. (1,000° F.), a hydrogen-to-hydrocarbon mole ratio of about 0 to about 20, a WHSV of about 0.01 hr$^{-1}$ to about 90 hr$^{-1}$, and a pressure of about 0 psig (101 kPa) to about 1,000 psig (6,998 kPa).

The following examples are being submitted to enable one skilled in the art to more easily and more clearly understand the present invention and are being submitted for the purpose of illustration only and are not intended to limit the scope of the present invention.

EXAMPLE I

An AMS-1B crystalline borosilicate molecular sieve was prepared. A 4.0-gm sample of sodium hydroxide and 10.0 gm of boric acid were dissolved in 600 gm of distilled water. To this solution were added 95.0 gm of tetrapropylammonium bromide. The tetrapropylammonium bromide was dissolved therein. Subsequently, 40 ml of concentrated ammonium hydroxide were added to and thoroughly dissolved in the solution. With vigorous agitation, 80.0 gm of Ludox HS-40 were added to the above solution and the resulting mixture was stirred for 20 minutes. The solution had a pH of 10.6. A 17.9-gm portion of sodium bisulfate was added to the solution to adjust the final pH of the solution to 10.0. The sodium bisulfate caused the solution to turn cloudy and become a slurry. The resulting slurry was then transferred into a one-liter crystallizer for crystallization at a temperature of about 165° C. (329° F.). The crystallization was performed over a period of one week. Then the material was removed from the crystallizer and the solid material was filtered from the crystallization solution. The solid filter cake was washed with approximately one liter of distilled water and dried on the filter. The solid material was then dried in a forced air oven overnight at a temperature of 165° C. (329° F.). The dried solid borosilicate was calcined in an oven in static air at a maximum rate of temperature increase of 111° C. (200° F.) per hour and then at a temperature of 538° C. (1,000° F.) for 4 hours. The temperature in the oven was then decreased at the same maximum rate of 200° F. per hour. The calcined solid was submitted for analysis by X-ray powder diffraction. The resulting X-ray diffraction pattern identified the material as AMS-1B crystalline borosilicate material. This crystalline borosilicate material is identified hereinafter as Borosilicate No. 1. Its X-ray diffraction pattern is presented hereinbelow in Table II.

TABLE II

X-RAY PATTERN FOR BOROSILICATE NO. 1

| d, Å | d, nm | I/I$_o$ | A.S. | Two-Theta |
|---|---|---|---|---|
| 11.32 | 1.132 | 71 | VS | 7.80 |
| 10.11 | 1.011 | 46 | MS | 8.73 |
| 6.01 | 0.601 | 21 | M | 14.72 |
| 5.60 | 0.560 | 14 | W | 15.80 |
| 5.01 | 0.501 | 11 | W | 17.67 |
| 4.27 | 0.427 | 15 | W | 20.80 |

TABLE II-continued

| X-RAY PATTERN FOR BOROSILICATE NO. 1 | | | | |
|---|---|---|---|---|
| d, Å | d, nm | I/I$_o$ | A.S. | Two-Theta |
| 4.01 | 0.401 | 16 | W | 22.14 |
| 3.84 | 0.384 | 100 | VS | 23.14 |
| 3.73 | 0.373 | 53 | MS | 23.83 |
| 3.65 | 0.365 | 40 | MS | 24.36 |
| 3.45 | 0.345 | 18 | W | 25.81 |
| 3.32 | 0.332 | 14 | W | 26.82 |
| 3.05 | 0.305 | 15 | W | 29.28 |
| 2.98 | 0.298 | 19 | W | 29.99 |
| 1.99 | 0.199 | 19 | W | 45.50 |

EXAMPLE II

In this example, an AMS-1B crystalline borosilicate was prepared by adding ammonium hydroxide just prior to crystallization.

An initial solution was prepared by dissolving 4.0 gm of sodium hydroxide and 10.0 gm of boric acid in 600 gm of distilled water. Subsequently, 95.0 gm of tetrapropylammonium bromide were dissolved in the solution. Then, 80.0 gm of Ludox HS-40 were thoroughly dispersed in the solution to form a uniform slurry. The pH of this slurry was adjusted to 10.0 by the addition of 0.4 gm of sodium hydroxide. The slurry was stirred for 20 minutes. To minimize the loss of ammonia, 20 ml of concentrated ammonium hydroxide (28–30% NH$_3$) were added to the slurry and the mixture was stirred for one minute before it was sealed in a one-liter bomb, which served as the crystallizer. The crystallization and the handling of the product were performed in the same manner as that described hereinabove in Example I. The resulting crystalline material, identified as AMS-1B crystalline borosilicate, is identified hereinafter as Borosilicate No. 2. The X-ray diffraction pattern of Borosilicate No. 2 is presented hereinafter in Table III.

TABLE III

| X-RAY PATTERN FOR BOROSILICATE NO. 2 | | | | |
|---|---|---|---|---|
| d, Å | d, nm | I/I$_o$ | A.S. | Two-Theta |
| 11.31 | 1.131 | 67 | MS | 7.81 |
| 10.10 | 1.010 | 43 | MS | 8.74 |
| 6.39 | 0.639 | 14 | W | 13.85 |
| 6.00 | 0.600 | 20 | M | 14.74 |
| 4.36 | 0.436 | 11 | W | 20.36 |
| 4.26 | 0.426 | 15 | W | 20.84 |
| 3.83 | 0.383 | 100 | VS | 23.18 |
| 3.72 | 0.372 | 51 | MS | 23.89 |
| 3.64 | 0.364 | 37 | M | 24.41 |
| 3.44 | 0.344 | 14 | W | 25.89 |
| 3.31 | 0.331 | 16 | W | 26.88 |
| 3.04 | 0.304 | 16 | W | 29.34 |
| 2.97 | 0.297 | 22 | M | 30.04 |
| 2.48 | 0.248 | 12 | W | 36.21 |
| 1.99 | 0.199 | 18 | W | 45.44 |
| 1.99 | 0.199 | 20 | M | 45.60 |

EXAMPLE III

In this example, a third AMS-1B crystalline borosilicate was prepared by employing a systematic decrease in the amount of sodium hydroxide that is used in the crystallization of the molecular sieve.

For this preparation, an initial solution was prepared by dissolving 3.0 gm of sodium hydroxide and 10.0 gm of boric acid in 600 gm of distilled water. To this solution, 95.0 gm of tetrapropylammonium bromide were added. After the tetrapropylammonium bromide was dissolved in the solution, 80 gm of Ludox HS-40 were added and the slurry that resulted was stirred for 20 minutes. The pH of this slurry was 9.5. To this slurry was added 40 ml of concentrated ammonium hydroxide with stirring for one minute. The slurry was immediately transferred to a one-liter bomb, which was employed as the crystallization vessel. The treatment of the slurry and the subsequent solid was the same as that described for Example I. The solid was identified as AMS-1B crystalline borosilicate by means of its X-ray diffraction pattern, which is presented hereinbelow in Table IV. The resulting crystalline borosilicate is identified hereinafter as Borosilicate No. 3.

TABLE IV

| X-RAY PATTERN FOR BOROSILICATE NO. 3 | | | | |
|---|---|---|---|---|
| d, Å | d, nm | I/I$_o$ | A.S. | Two-Theta |
| 11.30 | 1.130 | 79 | VS | 7.81 |
| 10.10 | 1.010 | 52 | MS | 8.74 |
| 6.00 | 0.600 | 23 | M | 14.74 |
| 5.69 | 0.569 | 13 | W | 15.55 |
| 5.01 | 0.501 | 12 | W | 17.70 |
| 4.36 | 0.436 | 10 | W | 20.35 |
| 4.26 | 0.426 | 15 | W | 20.83 |
| 3.83 | 0.383 | 100 | VS | 23.18 |
| 3.72 | 0.372 | 50 | MS | 23.87 |
| 3.64 | 0.364 | 38 | M | 24.41 |
| 3.44 | 0.344 | 13 | W | 25.88 |
| 3.31 | 0.331 | 15 | W | 26.87 |
| 3.04 | 0.304 | 17 | W | 29.32 |
| 2.97 | 0.297 | 22 | M | 30.03 |
| 2.48 | 0.248 | 12 | W | 36.19 |
| 1.99 | 0.199 | 22 | M | 45.60 |
| 1.66 | 0.166 | 11 | W | 55.46 |

EXAMPLE IV

In this example, an AMS-1B crystalline borosilicate was prepared by employing a further reduction in the amount of sodium hydroxide over that employed in Example III. The resulting borosilicate is identified hereinafter as Borosilicate No. 4.

Borosilicate No. 4 was prepared in a manner similar to that employed in Example III hereinabove; however, only 1.9 gm of sodium hydroxide were added and the pH prior to the addition of the ammonium hydroxide was 9.0. The resulting crystalline material was identified as AMS-1B borosilicate by means of its X-ray diffraction pattern, which is presented hereinafter in Table V.

TABLE V

| X-RAY PATTERN FOR BOROSILICATE NO. 4 | | | | |
|---|---|---|---|---|
| d, Å | d, nm | I/I$_o$ | A.S. | Two-Theta |
| 11.35 | 1.135 | 68 | MS | 7.78 |
| 10.13 | 1.013 | 48 | MS | 8.72 |
| 6.41 | 0.641 | 14 | W | 13.81 |
| 6.02 | 0.602 | 22 | M | 14.70 |
| 5.70 | 0.570 | 11 | W | 15.54 |
| 5.61 | 0.561 | 15 | W | 15.79 |
| 4.27 | 0.427 | 16 | W | 20.79 |
| 3.84 | 0.384 | 100 | VS | 23.13 |
| 3.73 | 0.373 | 47 | MS | 23.82 |
| 3.65 | 0.365 | 34 | M | 24.36 |
| 3.32 | 0.332 | 15 | W | 26.82 |
| 3.05 | 0.305 | 17 | W | 29.28 |
| 2.98 | 0.298 | 21 | M | 29.98 |
| 2.60 | 0.260 | 10 | W | 34.48 |
| 1.99 | 0.199 | 21 | M | 45.54 |

EXAMPLE V

In this example, another AMS-1B crystalline borosilicate was prepared. This borosilicate is identified hereinafter as Borosilicate No. 5. The sodium ions in the crystallization solution were replaced with tetramethylammonium cations; ammonium hydroxide was substituted for sodium hydroxide; and Ludox AS-40 was substituted for Ludox HS-40. Ludox AS-40 is an ammonium-ion-stabilized silicic acid sol, while Ludox HS-40 is a sodium-ion-stabilized silicic acid sol.

The crystallization solution was prepared by first dissolving 20.0 gm of boric acid in 1,200 gm of distilled water. To this initial solution, were added 200.0 gm of tetrapropylammonium bromide and 100 gm of tetramethylammonium chloride. Stirring was employed until all of the components were dissolved in the solution. Subsequently, 240 gm of Ludox AS-40 were added with vigorous stirring for 15 minutes. The pH of the resulting slurry was 7.4. Then 100 ml of concentrated ammonium hydroxide were added to the slurry and the resulting composite was stirred for 5 minutes. The crystallization slurry and the resulting solid were treated in a one-liter bomb as the crystallization vessel in the same manner as that employed in Example I. The resulting solid product was identified by X-ray diffraction analysis as AMS-1B crystalline borosilicate material. The X-ray diffraction pattern for Borosilicate No. 5 is presented hereinafter in Table VI.

TABLE VI

| X-RAY PATTERN FOR BOROSILICATE NO. 5 | | | | |
|---|---|---|---|---|
| d, Å | d, nm | I/I$_o$ | A.S. | Two-Theta |
| 11.34 | 1.134 | 80 | VS | 7.79 |
| 10.12 | 1.012 | 56 | MS | 8.72 |
| 6.40 | 0.640 | 15 | W | 13.81 |
| 6.01 | 0.601 | 24 | M | 14.71 |
| 5.70 | 0.570 | 13 | W | 15.52 |
| 5.60 | 0.560 | 16 | W | 15.80 |
| 5.01 | 0.501 | 12 | W | 17.67 |
| 4.27 | 0.427 | 17 | W | 20.80 |
| 3.84 | 0.384 | 100 | VS | 23.14 |
| 3.73 | 0.373 | 48 | MS | 23.82 |
| 3.65 | 0.365 | 35 | M | 24.37 |
| 3.44 | 0.344 | 14 | W | 25.85 |
| 3.32 | 0.332 | 15 | W | 26.83 |
| 3.05 | 0.305 | 17 | W | 29.28 |
| 2.98 | 0.298 | 21 | M | 29.99 |
| 2.60 | 0.260 | 10 | W | 34.46 |
| 2.48 | 0.248 | 12 | W | 36.13 |
| 2.00 | 0.200 | 17 | W | 45.32 |
| 1.99 | 0.199 | 21 | M | 45.55 |

EXAMPLES VI-IX

In these four examples, Ludox AS-40, the ammonium-ion-stabilized silicic acid sol, was employed. No sodium hydroxide was used. The substitution of the Ludox AS-40 for Ludox HS-40 and the elimination of sodium hydroxide from the crystallization solution minimized the contamination of the resulting borosilicate with sodium. Each of these borosilicates was prepared according to the method described in Example V. The quantity of materials for each preparation is shown in Table VII hereinbelow. Each crystallization solution was digested for 7 days at 165° C. (329° F.). The treatment of the crystalline solid was similar to that employed in Example I.

TABLE VII

| BOROSILICATE PREPARATION DATA | | | | |
|---|---|---|---|---|
| Example | VI | VII | VIII | IX |
| Borosilicate No. | 6 | 7 | 8 | 9 |
| Dist. Water, gm | 600.0 | 600.0 | 600.0 | 600.0 |
| H$_3$BO$_3$, gm | 10.0 | 20.0 | 20.0 | 20.0 |
| TPABr, gm | 95.0 | 95.0 | 95.0 | 95.0 |
| Ludox AS-40, gm | 40.0 | 40.0 | 40.0 | 40.0 |

TABLE VII-continued

| BOROSILICATE PREPARATION DATA | | | | |
|---|---|---|---|---|
| Example | VI | VII | VIII | IX |
| pH after 15 min. stirring | 6.8 | 5.9 | 5.7 | 5.8 |
| Conc. NH$_4$OH, ml | 40.0 | 60.0 | 40.0 | 40.0 |

TABLE VIII

| X-RAY PATTERN FOR BOROSILICATE NO. 6 | | | | |
|---|---|---|---|---|
| d, Å | d, nm | I/I$_o$ | A.S. | Two-Theta |
| 11.32 | 1.132 | 77 | VS | 7.80 |
| 10.11 | 0.011 | 57 | MS | 8.74 |
| 6.01 | 0.601 | 24 | M | 14.73 |
| 5.69 | 0.569 | 13 | W | 15.55 |
| 5.60 | 0.560 | 16 | W | 15.80 |
| 5.01 | 0.501 | 18 | W | 17.67 |
| 4.62 | 0.462 | 14 | W | 19.18 |
| 4.26 | 0.426 | 16 | W | 20.82 |
| 3.84 | 0.384 | 100 | VS | 23.16 |
| 3.73 | 0.373 | 49 | MS | 23.83 |
| 3.65 | 0.365 | 34 | M | 24.38 |
| 3.44 | 0.344 | 13 | W | 25.85 |
| 3.32 | 0.332 | 15 | W | 26.84 |
| 3.05 | 0.305 | 17 | W | 29.30 |
| 2.98 | 0.298 | 21 | M | 30.00 |
| 2.60 | 0.260 | 10 | W | 34.47 |
| 2.48 | 0.248 | 12 | W | 36.16 |
| 2.00 | 0.200 | 17 | W | 45.30 |
| 1.99 | 0.199 | 21 | M | 45.57 |

TABLE IX

| X-RAY PATTERN FOR BOROSILICATE NO. 7 | | | | |
|---|---|---|---|---|
| d, Å | d, nm | I/I$_o$ | A.S. | Two-Theta |
| 11.34 | 1.134 | 78 | VS | 7.79 |
| 10.13 | 1.013 | 54 | MS | 8.72 |
| 6.41 | 0.641 | 15 | W | 13.81 |
| 6.02 | 0.602 | 23 | M | 14.70 |
| 5.69 | 0.569 | 11 | W | 15.54 |
| 5.61 | 0.561 | 15 | W | 15.79 |
| 5.02 | 0.502 | 11 | W | 17.66 |
| 4.27 | 0.427 | 16 | W | 20.79 |
| 3.84 | 0.384 | 100 | VS | 23.12 |
| 3.73 | 0.373 | 46 | MS | 23.81 |
| 3.65 | 0.365 | 32 | MS | 24.35 |
| 3.32 | 0.332 | 15 | W | 26.81 |
| 3.05 | 0.305 | 16 | W | 29.27 |
| 2.98 | 0.298 | 21 | M | 29.97 |
| 2.48 | 0.248 | 12 | W | 36.11 |
| 2.21 | 0.221 | 13 | W | 40.86 |
| 1.99 | 0.199 | 20 | M | 45.50 |

TABLE X

| X-RAY PATTERN FOR BOROSILICATE NO. 8 | | | | |
|---|---|---|---|---|
| d, Å | d, nm | I/I$_o$ | A.S. | Two-Theta |
| 11.41 | 1.114 | 57 | MS | 7.74 |
| 10.18 | 1.018 | 44 | MS | 8.67 |
| 6.43 | 0.643 | 13 | W | 13.75 |
| 6.04 | 0.604 | 21 | M | 14.65 |
| 4.28 | 0.428 | 15 | W | 20.73 |
| 3.85 | 0.385 | 100 | VS | 23.06 |
| 3.74 | 0.374 | 48 | MS | 23.76 |
| 3.66 | 0.366 | 34 | M | 24.29 |
| 3.45 | 0.345 | 13 | W | 25.77 |
| 3.33 | 0.333 | 16 | W | 26.74 |
| 3.05 | 0.305 | 17 | W | 29.21 |
| 2.98 | 0.298 | 22 | M | 29.91 |
| 1.99 | 0.199 | 21 | M | 45.46 |
| 1.66 | 0.166 | 12 | W | 55.24 |

TABLE XI

X-RAY PATTERN FOR BOROSILICATE NO. 9

| d, Å | d, nm | $I/I_o$ | A.S. | Two-Theta |
|------|-------|---------|------|-----------|
| 11.38 | 1.138 | 71 | VS | 7.76 |
| 10.16 | 1.016 | 56 | MS | 8.70 |
| 6.42 | 0.642 | 14 | W | 13.79 |
| 6.03 | 0.603 | 23 | M | 14.68 |
| 5.61 | 0.561 | 15 | W | 15.77 |
| 4.27 | 0.427 | 15 | W | 20.76 |
| 3.85 | 0.385 | 100 | VS | 23.10 |
| 3.74 | 0.374 | 47 | MS | 23.78 |
| 3.66 | 0.366 | 33 | M | 24.32 |
| 3.33 | 0.333 | 15 | W | 26.78 |
| 3.05 | 0.305 | 16 | W | 29.23 |
| 2.98 | 0.298 | 21 | M | 29.94 |
| 2.49 | 0.249 | 12 | W | 36.07 |
| 1.99 | 0.199 | 20 | M | 45.48 |

EXAMPLE X

Another embodiment of AMS-1B crystalline borosilicate was prepared. This borosilicate is identified hereinafter as Borosilicate No. 10.

For the preparation of Borosilicate No. 10, 287 gm of Ludox HS-40 were added to a solution in a one-gallon (3.79-1) Waring Blendor, which solution had been prepared by dissolving 51 gm of boric acid, 310 gm of tetrapropylammonium bromide, and 400 gm of (28%–30% NH$_3$) ammonium hydroxide in 1,700 gm of distilled water. The solution was stirred at a high stirring rate for 10 minutes. Then it was placed in a three-liter autoclave and heated at a temperature of 165° C. (329° F.) for 6 days. The material was removed from the autoclave on the seventh day. The crystalline material was isolated by filtration, washed with 10 liters of distilled water, and dried in a forced air oven overnight at a temperature of 165° C. (329° F.). The dried solid borosilicate was calcined in an oven at a temperature of 538° C. (1,000° F.) for 12 hours after the temperature had been increased at a maximum rate of 111° C. (200° F.) per hour.

The crystalline material obtained from this preparation was found to have the X-ray pattern that is presented in Table XII hereinbelow, which X-ray diffraction pattern identifies the material as a borosilicate. The material was found to have the following molar composition: 0.04 Na$_2$O:B$_2$O$_3$:57.8 SiO$_2$.

TABLE XII

X-RAY PATTERN FOR BOROSILICATE NO. 10

| d, Å | d, nm | $I/I_o$ | A.S. | Two-Theta |
|------|-------|---------|------|-----------|
| 11.11 | 1.111 | 40 | MS | 7.95 |
| 9.94 | 0.994 | 34 | M | 8.89 |
| 6.66 | 0.666 | 6 | VW | 13.28 |
| 6.32 | 0.632 | 12 | W | 14.00 |
| 5.94 | 0.594 | 17 | W | 14.89 |
| 5.54 | 0.554 | 12 | W | 15.99 |
| 4.96 | 0.496 | 9 | VW | 17.85 |
| 4.57 | 0.457 | 8 | VW | 19.38 |
| 4.33 | 0.433 | 10 | W | 20.51 |
| 4.23 | 0.423 | 15 | W | 20.99 |
| 3.97 | 0.397 | 10 | W | 22.35 |
| 3.81 | 0.381 | 100 | VS | 23.33 |
| 3.70 | 0.370 | 47 | MS | 24.02 |
| 3.62 | 0.362 | 36 | M | 24.56 |
| 3.42 | 0.342 | 14 | W | 26.06 |
| 3.30 | 0.330 | 15 | W | 27.03 |
| 3.22 | 0.322 | 8 | VW | 27.64 |
| 3.12 | 0.312 | 7 | VW | 28.58 |
| 3.03 | 0.303 | 18 | W | 29.49 |
| 2.96 | 0.296 | 21 | M | 30.20 |
| 2.84 | 0.284 | 6 | VW | 31.43 |
| 2.71 | 0.271 | 9 | VW | 33.02 |
| 2.58 | 0.258 | 10 | W | 34.68 |
| 2.55 | 0.255 | 8 | VW | 35.10 |
| 2.47 | 0.247 | 11 | W | 36.35 |
| 2.38 | 0.238 | 10 | W | 37.79 |
| 2.31 | 0.231 | 6 | VW | 39.04 |
| 2.09 | 0.209 | 6 | VW | 43.23 |
| 2.06 | 0.206 | 7 | VW | 43.90 |
| 1.98 | 0.198 | 21 | M | 45.78 |
| 1.94 | 0.194 | 9 | VW | 46.83 |
| 1.90 | 0.190 | 10 | W | 47.83 |
| 1.86 | 0.186 | 10 | W | 49.01 |
| 1.81 | 0.181 | 7 | VW | 50.27 |
| 1.75 | 0.175 | 8 | VW | 52.28 |
| 1.70 | 0.170 | 6 | VW | 53.84 |
| 1.69 | 0.169 | 5 | VW | 54.29 |
| 1.65 | 0.165 | 11 | W | 55.69 |
| 1.63 | 0.163 | 6 | VW | 56.46 |
| 1.61 | 0.161 | 6 | VW | 57.14 |
| 1.60 | 0.160 | 7 | VW | 57.60 |
| 1.55 | 0.155 | 7 | VW | 59.53 |
| 1.51 | 0.151 | 6 | VW | 61.48 |

EXAMPLE XI

Another AMS-1B crystalline borosilicate was prepared according to the preparation method described hereinabove in Example X. However, there were several variations from the preparation in Example X. For this example, 363 gm of ammonium hydroxide and 1,800 gm of distilled water were used. The solution was heated for 7 days in the autoclave and the contents were removed from the autoclave on the eighth day. The crystalline material that was obtained from this preparation was found to have the X-ray pattern shown hereinbelow in Table XIII, which X-ray diffraction pattern identifies it as an AMS-1B crystalline borosilicate. It is identified hereinafter as Borosilicate No. 11 and was found to have the following molar composition: 0.03 Na$_2$O:B$_2$O$_3$:51.7 SiO$_2$.

TABLE XIII

X-RAY PATTERN FOR BOROSILICATE NO. 11

| d, Å | d, nm | $I/I_o$ | A.S. | Two-Theta |
|------|-------|---------|------|-----------|
| 11.09 | 1.109 | 37 | M | 7.96 |
| 9.93 | 0.993 | 31 | M | 8.90 |
| 6.65 | 0.665 | 6 | VW | 13.30 |
| 6.32 | 0.632 | 11 | W | 14.01 |
| 5.94 | 0.594 | 15 | W | 14.90 |
| 5.64 | 0.564 | 10 | W | 15.69 |
| 5.53 | 0.553 | 12 | W | 16.00 |
| 4.96 | 0.496 | 9 | VW | 17.87 |
| 4.57 | 0.457 | 8 | VW | 19.40 |
| 4.32 | 0.432 | 10 | W | 20.52 |
| 4.22 | 0.422 | 16 | MW | 21.01 |
| 3.97 | 0.397 | 9 | VW | 22.37 |
| 3.81 | 0.381 | 100 | VS | 23.35 |
| 3.70 | 0.370 | 46 | MS | 24.04 |
| 3.62 | 0.362 | 36 | M | 24.58 |
| 3.41 | 0.341 | 14 | W | 26.07 |
| 3.29 | 0.329 | 15 | W | 27.04 |
| 3.22 | 0.322 | 8 | VW | 27.65 |
| 3.12 | 0.312 | 7 | VW | 28.63 |
| 3.02 | 0.302 | 18 | W | 29.51 |
| 2.95 | 0.295 | 22 | M | 30.22 |
| 2.84 | 0.284 | 7 | VW | 31.47 |
| 2.76 | 0.276 | 5 | VW | 32.40 |
| 2.71 | 0.271 | 9 | VW | 33.04 |
| 2.58 | 0.258 | 11 | W | 34.71 |
| 2.56 | 0.256 | 8 | VW | 35.06 |
| 2.47 | 0.247 | 12 | W | 36.39 |
| 2.42 | 0.242 | 5 | VW | 37.04 |
| 2.38 | 0.238 | 10 | W | 37.80 |
| 2.09 | 0.209 | 6 | VW | 43.19 |

TABLE XIII-continued

X-RAY PATTERN FOR BOROSILICATE NO. 11

| d, Å | d, nm | I/I$_o$ | A.S. | Two-Theta |
|------|-------|---------|------|-----------|
| 2.06 | 0.206 | 7 | VW | 43.97 |
| 1.98 | 0.198 | 21 | M | 45.80 |
| 1.94 | 0.194 | 9 | VW | 46.86 |
| 1.90 | 0.190 | 10 | W | 47.84 |
| 1.86 | 0.186 | 10 | W | 49.03 |
| 1.82 | 0.182 | 6 | VW | 50.18 |
| 1.75 | 0.175 | 8 | VW | 52.33 |
| 1.70 | 0.170 | 6 | VW | 53.89 |
| 1.65 | 0.165 | 11 | W | 55.65 |
| 1.61 | 0.161 | 7 | VW | 57.17 |
| 1.60 | 0.160 | 7 | VW | 57.60 |
| 1.55 | 0.155 | 7 | VW | 59.53 |
| 1.53 | 0.153 | 5 | VW | 60.66 |
| 1.51 | 0.151 | 6 | VW | 61.48 |

EXAMPLE XII

Another embodiment of AMS-1B crystalline borosilicate material was prepared, but this time Ludox AS-40 was used.

For this preparation, 287 gm of Ludox AS-40 were added to a one-gallon (3.79 l) Waring Blendor containing a solution that had been prepared by dissolving 53 gm of boric acid, 310 gm of tetrapropylammonium bromide, and 380 gm of (28%–30%) NH$_4$OH in 1,800 gm of distilled water. The resulting solution was stirred at high speed for 10 minutes, after which an additional 94 gm of (28%–30%) NH$_4$OH were added. Stirring was continued for about 2 to 3 minutes. The solution was then placed in a three-liter autoclave and heated at a temperature of 165° C. (329° F.) for 6 days. The contents of the autoclave were removed on the seventh day. The crystalline material was isolated by filtration, washed with 9 liters of distilled water, and dried at 165° C. (329° F.). The dried solid was calcined overnight at a temperature of 538° C. (1,000° F.). This crystalline material, identified as crystalline borosilicate, was found to have the X-ray diffraction pattern that is presented hereinafter in Table XIV. This crystalline borosilicate is identified hereinafter as Borosilicate No. 12. Its composition was found to be: 0.07 Na$_2$O:B$_2$O$_3$:69.5 SiO$_2$.

TABLE XIV

X-RAY PATTERN FOR BOROSILICATE NO. 12

| d, Å | d, nm | I/I$_o$ | A.S. | Two-Theta |
|------|-------|---------|------|-----------|
| 11.11 | 1.111 | 34 | M | 7.95 |
| 9.93 | 0.993 | 28 | M | 8.89 |
| 6.66 | 0.666 | 6 | VW | 13.28 |
| 6.32 | 0.632 | 10 | W | 14.00 |
| 5.94 | 0.594 | 13 | W | 14.89 |
| 5.62 | 0.562 | 8 | VW | 15.75 |
| 5.54 | 0.554 | 12 | W | 15.99 |
| 4.96 | 0.496 | 8 | VW | 17.87 |
| 4.57 | 0.457 | 8 | VW | 19.39 |
| 4.32 | 0.432 | 11 | W | 20.52 |
| 4.23 | 0.423 | 16 | W | 20.99 |
| 3.97 | 0.397 | 9 | VW | 22.36 |
| 3.81 | 0.381 | 100 | VS | 23.34 |
| 3.70 | 0.370 | 46 | MS | 24.03 |
| 3.62 | 0.362 | 37 | M | 24.58 |
| 3.42 | 0.342 | 14 | W | 26.06 |
| 3.29 | 0.329 | 15 | W | 27.05 |
| 3.22 | 0.322 | 9 | VW | 27.64 |
| 3.12 | 0.312 | 8 | VW | 28.60 |
| 3.03 | 0.303 | 19 | W | 29.50 |
| 2.95 | 0.295 | 22 | M | 30.22 |
| 2.84 | 0.284 | 7 | VW | 31.47 |
| 2.71 | 0.271 | 11 | W | 33.03 |
| 2.58 | 0.258 | 10 | W | 34.72 |
| 2.56 | 0.256 | 8 | VW | 35.06 |
| 2.47 | 0.247 | 12 | W | 36.37 |

TABLE XIV-continued

X-RAY PATTERN FOR BOROSILICATE NO. 12

| d, Å | d, nm | I/I$_o$ | A.S. | Two-Theta |
|------|-------|---------|------|-----------|
| 2.38 | 0.238 | 10 | W | 37.78 |
| 2.30 | 0.230 | 6 | VW | 39.04 |
| 2.09 | 0.209 | 6 | VW | 43.24 |
| 2.06 | 0.206 | 7 | VW | 43.97 |
| 1.98 | 0.198 | 21 | M | 45.80 |
| 1.94 | 0.194 | 9 | VW | 46.81 |
| 1.90 | 0.190 | 10 | W | 47.84 |
| 1.86 | 0.186 | 11 | W | 49.01 |
| 1.81 | 0.181 | 7 | VW | 50.23 |
| 1.75 | 0.175 | 8 | VW | 52.25 |
| 1.70 | 0.170 | 6 | VW | 53.86 |
| 1.65 | 0.165 | 12 | W | 55.67 |
| 1.61 | 0.161 | 6 | VW | 57.24 |
| 1.60 | 0.160 | 7 | VW | 57.58 |
| 1.55 | 0.155 | 7 | VW | 59.52 |
| 1.51 | 0.151 | 6 | VW | 61.49 |

EXAMPLE XIII

A sample of Borosilicate No. 11 was analyzed for its X-ray powder diffraction pattern employing a slower scanning speed while the data were corrected with an external silica standard, Arkansas stone. The normal scanning speed is 2° 2θ per minute. The slower scanning speed employed in X-ray analysis of this sample was 0.25° 2θ per minute. The resulting X-ray powder diffraction pattern is presented hereinafter in Table XV.

TABLE XV

ADDITIONAL X-RAY DATA FOR BOROSILICATE NO. 11

| d, Å | d, nm | I/I$_o$ | A.S. | Two-Theta |
|------|-------|---------|------|-----------|
| 11.04 | 1.104 | 21 | M | 8.02 |
| 9.91 | 0.991 | 13 | W | 8.92 |
| 9.62 | 0.962 | 4 | VW | 9.19 |
| 6.64 | 0.664 | 5 | VW | 13.33 |
| 6.31 | 0.631 | 10 | W | 14.04 |
| 5.94 | 0.594 | 11 | W | 14.91 |
| 5.67 | 0.567 | 10 | W | 15.63 |
| 5.53 | 0.553 | 10 | W | 16.04 |
| 4.96 | 0.496 | 6 | VW | 17.87 |
| 4.57 | 0.457 | 6 | VW | 19.41 |
| 4.33 | 0.433 | 10 | W | 20.52 |
| 4.22 | 0.422 | 15 | W | 21.03 |
| 3.97 | 0.397 | 9 | VW | 22.38 |
| 3.82 | 0.382 | 100 | VS | 23.29 |
| 3.79 | 0.379 | 74 | VS | 23.47 |
| 3.72 | 0.372 | 35 | M | 23.90 |
| 3.69 | 0.369 | 48 | MS | 24.14 |
| 3.63 | 0.363 | 36 | M | 24.51 |
| 3.46 | 0.346 | 7 | VW | 25.77 |
| 3.41 | 0.341 | 12 | W | 26.11 |
| 3.32 | 0.332 | 10 | W | 26.88 |
| 3.29 | 0.329 | 13 | W | 27.11 |
| 3.23 | 0.323 | 5 | VW | 27.66 |
| 3.12 | 0.312 | 4 | VW | 28.65 |
| 3.03 | 0.303 | 15 | W | 29.52 |
| 2.96 | 0.296 | 16 | W | 30.19 |
| 2.92 | 0.292 | 10 | W | 30.62 |
| 2.84 | 0.284 | 4 | VW | 31.46 |
| 2.71 | 0.271 | 7 | VW | 33.05 |
| 2.59 | 0.259 | 8 | VW | 34.65 |
| 2.50 | 0.250 | 6 | VW | 36.00 |
| 2.47 | 0.247 | 9 | VW | 36.37 |
| 2.40 | 0.240 | 5 | VW | 37.51 |
| 2.38 | 0.238 | 6 | VW | 37.84 |
| 2.00 | 0.200 | 17 | W | 45.43 |
| 1.98 | 0.198 | 16 | W | 45.81 |
| 1.94 | 0.194 | 5 | VW | 46.89 |
| 1.90 | 0.190 | 6 | VW | 47.85 |
| 1.86 | 0.186 | 7 | VW | 49.00 |

EXAMPLE XIV

Each of Borosilicates Nos. 10, 11, and 12 was mixed with PHF-alumina sol that had been obtained from the American Cyanamid Company. The alumina sol contained 9 wt.% solids.

In each case, a 15-gram portion of the respective borosilicate was mixed with 167 gm of the alumina sol in a Waring Blendor. The mixture was gelled by the addition of 10 ml of 14% ammonium hydroxide solution. The gel was dried at a temperature of 165° C. (329° F.) for about 20 hours and calcined overnight at a temperature of 538° C. (1,000° F.).

The Borosilicates Nos. 10, 11, and 12 were employed to make Catalysts Nos. 1, 2, and 3, respectively. In each case, the resultant catalyst was ground to a mesh size of 18-to-40 mesh (1.00 mm-to-0.419 mm) material, i.e., ground to pass through an 18-mesh (1.00 mm) screen (U.S. Sieve Series) but be retained upon a 40-mesh (0.419 mm) screen. For each test, 7 gm of the ground particles were employed.

Each catalyst was loaded into a tubular reactor having an inside diameter of 0.59 inch (1.5 cm). The catalysts were tested for their ability to isomerize a xylene feed having the composition shown hereinafter in Table XVI.

Each of the tests was conducted in the presence of hydrogen at a temperature of 399° C. (750° F.). The liquid feed rate varied from about 47 to 63 gm/hr. Additional test conditions, as well as test results, for each of these tests are presented hereinbelow in Table XVI. Catalysts Nos. 1, 2, and 3 were tested in Tests Nos. 1, 2, and 3, respectively. The data from these tests demonstrate that the Catalysts Nos. 1, 2, and 3 are suitable for the isomerization of xylene feedstocks.

TABLE XVI
DATA FROM XYLENE-ISOMERIZATION TESTS

| TEST CONDITIONS | TEST 1 | TEST 2 | TEST 3 |
|---|---|---|---|
| Temperature | | | |
| °C. | 399 | 399 | 399 |
| °F. | 750 | 750 | 750 |
| Pressure | | | |
| psig | 200 | 200 | 200 |
| kPa | 1472 | 1472 | 1472 |
| $H_2$/HC | 8.1 | 5.2 | 4.8 |
| Contact Time, | | | |
| sec | 5.1 | 4.9 | 4.7 |
| Hours on Oil | 6 | 6 | 6 |

| COMPONENT, | PRODUCTS FROM | | | |
|---|---|---|---|---|
| WT. % | FEED | TEST 1 | TEST 2 | TEST 3 |
| Benzene | — | 2.07 | 1.31 | 0.90 |
| Toluene | 0.04 | 0.47 | 0.26 | 0.15 |
| Ethylbenzene | 19.38 | 15.49 | 16.71 | 17.23 |
| Para-Xylene | 9.43 | 18.91 | 19.09 | 18.36 |
| Meta-Xylene | 47.18 | 41.55 | 42.03 | 42.27 |
| Ortho-Xylene | 23.88 | 17.99 | 18.39 | 19.75 |
| $C_9$ and $C_{10}$ Aromatics | 0.09 | 3.52 | 2.21 | 1.34 |

| % APPROACH TO EQUILIBRIUM | TEST 1 | TEST 2 | TEST 3 |
|---|---|---|---|
| Para-Xylene | 104.8 | 104.0 | 94.0 |
| Meta-Xylene | 91.2 | 92.3 | 97.2 |
| Ortho-Xylene | 119.5 | 116.0 | 90.4 |
| Ethylbenzene | 22.5 | 15.8 | 13.5 |
| % Ethylbenzene Conversion/pass | 20.0 | 13.8 | 11.1 |
| % Xylene Loss/pass | 2.5 | 1.2 | 0.2 |

A summary of the X-ray diffraction patterns for the various crystalline AMS-1B borosilicates obtained in the preceding examples is presented in Table XVII hereinbelow. In each instance, the borosilicate had been calcined at a temperature of 538° C. (1,000° F.). It can be seen that each pattern follows closely the lines and assigned strengths set forth for crystalline AMS-1B borosilicates in co-pending application United States Ser. No. 897,360.

TABLE XVII
X-RAY PATTERN SUMMARY

| BOROSILICATE NO. | 1 | | |
|---|---|---|---|
| EXAMPLE NO. | I | | |
| X-RAY PATTERN | d, Å | d, nm | A.S. |
| | 11.32 | 1.132 | VS |
| | 10.11 | 1.011 | MS |
| | 6.01 | 0.601 | M |
| | 3.84 | 0.384 | VS |
| | 3.73 | 0.373 | MS |
| | 3.65 | 0.365 | MS |
| | 2.98 | 0.298 | W |
| | 1.99 | 0.199 | W |

| BOROSILICATE NO. | 2 | | |
|---|---|---|---|
| EXAMPLE NO. | II | | |
| X-RAY PATTERN | d, Å | d, nm | A.S. |
| | 11.31 | 1.131 | MS |
| | 10.10 | 1.010 | MS |
| | 6.00 | 0.600 | M |
| | 3.83 | 0.383 | VS |
| | 3.72 | 0.372 | MS |
| | 3.64 | 0.364 | M |
| | 2.97 | 0.297 | M |
| | 1.99 | 0.199 | W |

| BOROSILICATE NO. | 3 | | |
|---|---|---|---|
| EXAMPLE NO. | III | | |
| X-RAY PATTERN | d, Å | d, nm | A.S. |
| | 11.30 | 1.130 | VS |
| | 10.10 | 1.010 | MS |
| | 6.00 | 0.600 | M |
| | 3.83 | 0.383 | VS |
| | 3.72 | 0.372 | MS |
| | 3.64 | 0.364 | M |
| | 2.97 | 0.297 | M |
| | 1.99 | 0.199 | M |

| BOROSILICATE NO. | 4 | | |
|---|---|---|---|
| EXAMPLE NO. | IV | | |
| X-RAY PATTERN | d, Å | d, nm | A.S. |
| | 11.35 | 1.135 | MS |
| | 10.13 | 1.013 | MS |
| | 6.02 | 0.602 | M |
| | 3.84 | 0.384 | VS |
| | 3.73 | 0.373 | MS |
| | 3.65 | 0.365 | M |
| | 2.98 | 0.298 | M |
| | 1.99 | 0.199 | M |

| BOROSILICATE NO. | 5 | | |
|---|---|---|---|
| EXAMPLE NO. | V | | |
| X-RAY PATTERN | d, Å | d, nm | A.S. |
| | 11.34 | 1.134 | VS |
| | 10.12 | 1.012 | MS |
| | 6.01 | 0.601 | M |
| | 3.84 | 0.384 | VS |
| | 3.73 | 0.373 | MS |
| | 3.65 | 0.365 | M |
| | 2.98 | 0.298 | M |
| | 1.99 | 0.199 | M |

| BOROSILICATE NO. | 6 | | |
|---|---|---|---|
| EXAMPLE NO. | VI | | |
| X-RAY PATTERN | d, Å | d, nm | A.S. |
| | 11.32 | 1.132 | VS |
| | 10.11 | 1.011 | MS |
| | 6.01 | 0.601 | M |
| | 3.84 | 0.384 | VS |
| | 3.73 | 0.373 | MS |
| | 3.65 | 0.365 | M |
| | 2.98 | 0.298 | M |

TABLE XVII-continued

X-RAY PATTERN SUMMARY

| | 1.99 | 0.199 | M |
|---|---|---|---|

| BOROSILICATE NO. | 7 | | |
|---|---|---|---|
| EXAMPLE NO. | VII | | |
| X-RAY PATTERN | d, Å | d, nm | A.S. |
| | 11.34 | 1.134 | VS |
| | 10.13 | 1.013 | MS |
| | 6.02 | 0.602 | M |
| | 3.84 | 0.384 | VS |
| | 3.73 | 0.373 | MS |
| | 3.65 | 0.365 | MS |
| | 2.98 | 0.298 | M |
| | 1.99 | 0.199 | M |

| BOROSILICATE NO. | 8 | | |
|---|---|---|---|
| EXAMPLE NO. | VIII | | |
| X-RAY PATTERN | d, Å | d, nm | A.S. |
| | 11.41 | 1.141 | MS |
| | 10.18 | 1.018 | MS |
| | 6.04 | 0.604 | M |
| | 3.85 | 0.385 | VS |
| | 3.74 | 0.374 | MS |
| | 3.66 | 0.366 | MS |
| | 2.98 | 0.298 | M |
| | 1.99 | 0.199 | M |

| BOROSILICATE NO. | 9 | | |
|---|---|---|---|
| EXAMPLE NO. | IX | | |
| X-RAY PATTERN | d, Å | d, nm | A.S. |
| | 11.38 | 1.138 | VS |
| | 10.16 | 1.016 | MS |
| | 6.03 | 0.603 | M |
| | 3.85 | 0.385 | VS |
| | 3.74 | 0.374 | MS |
| | 3.66 | 0.366 | M |
| | 2.98 | 0.298 | M |
| | 1.99 | 0.199 | M |

| BOROSILICATE NO. | 10 | | |
|---|---|---|---|
| EXAMPLE NO. | X | | |
| X-RAY PATTERN | d, Å | d, nm | A.S. |
| | 11.11 | 1.111 | MS |
| | 9.94 | 0.994 | M |
| | 5.94 | 0.594 | W |
| | 3.81 | 0.381 | VS |
| | 3.70 | 0.370 | MS |
| | 3.62 | 0.362 | M |
| | 2.96 | 0.296 | M |
| | 1.98 | 0.198 | M |

| BOROSILICATE NO. | 11 | | |
|---|---|---|---|
| EXAMPLE NO. | XI | | |
| X-RAY PATTERN | d, Å | d, nm | A.S. |
| | 11.09 | 1.109 | M |
| | 9.93 | 0.993 | M |
| | 5.94 | 0.594 | W |
| | 3.81 | 0.381 | VS |
| | 3.70 | 0.370 | MS |
| | 3.62 | 0.362 | M |
| | 2.95 | 0.295 | M |
| | 1.98 | 0.198 | M |

| BOROSILICATE NO. | 12 | | |
|---|---|---|---|
| EXAMPLE NO. | XII | | |
| X-RAY PATTERN | d, Å | d, nm | A.S. |
| | 11.11 | 1.111 | M |
| | 9.93 | 0.993 | M |
| | 5.94 | 0.594 | W |
| | 3.81 | 0.381 | VS |
| | 3.70 | 0.370 | MS |
| | 3.62 | 0.362 | M |
| | 2.95 | 0.295 | M |
| | 1.98 | 0.198 | M |

EXAMPLE XV

Thirteen samples of borosilicates were prepared in the presence of low ammonium hydroxide concentrations to determine the minimum amount of concentrated ammonium hydroxide that must be added during the preparation of the borosilicate to obtain a crystalline material.

In the case of each of the preparations discussed in this example, the quantities of chemicals that were employed during the preparations are shown hereinafter in Table XVIII. The various reactants were added in the descending order shown. The crystallizations were performed at 165° C. (329° F.) in a stirred 2-liter Parr reactor for either four or five days. The handling of the products was performed in the same manner as that described in Example I with the exception that two liters of wash water were employed rather than one liter and the drying temperature was 110° C. (230° F.). The results of these tests suggest that a combination of 10 ml of concentrated ammonium hydroxide and 320 gm of Ludox AS-40 will provide a suitable crystalline product and that a minimum ratio of ml of concentrated ammonium hydroxide to Ludox is needed.

TABLE XVIII

PREPARATION INFORMATION - PREPARATIONS AT LOW AMMONIUM HYDROXIDE CONCENTRATIONS

| REACTANT | PREPARATION NO. | | | | | | | | | | | | |
|---|---|---|---|---|---|---|---|---|---|---|---|---|---|
| | 15 | 16 | 17 | 18 | 19 | 20 | 21 | 22 | 23 | 24 | 25 | 26 | 27 |
| DIST. WATER, gm | 1,200 | 1,200 | 1,200 | 1,200 | 1,200 | 1,200 | 1,200 | 1,200 | 1,200 | 1,200 | 1,200 | 1,200 | 1,200 |
| $H_3BO_3$, gm | 20.0 | 20.0 | 20.0 | 20.0 | 20.0 | 20.0 | 20.0 | 20.0 | 20.0 | 20.0 | 40.0 | 40.0 | 40.0 |
| CONC. $NH_4OH$, ml | 10 | 5 | 10 | 20 | 40 | 5 | 10 | 20 | 40 | 80 | 78 | 88 | 108 |
| TPABr[1], gm | 190.0 | 190.0 | 190.0 | 190.0 | 190.0 | 190.0 | 190.0 | 190.0 | 190.0 | 190.0 | 190.0 | 190.0 | 190.0 |
| LUDOX, AS-40, gm. | 80.0 | 80.8 | 81.0 | 80.9 | 82.7 | 321.3 | 321.1 | 320.3 | 321.8 | 319.5 | 321.0 | 323.0 | 321.4 |
| pH[2] | 8.86 | 8.41 | 9.13 | 9.58 | 9.94 | 8.43 | 8.92 | 9.30 | 9.64 | 9.97 | 9.82 | 9.88 | 9.99 |
| CRYSTALLINITY, % | AMORPHOUS[3] | 100 | 100 | 100 | 100 | 40 | 100 | 100 | 100 | 95+ | 100 | 100 | 100 |
| HOURS AT 165° C. | 40 | 112 | 136 | 136 | 136 | 112 | 112 | 64 | 64 | 64 | 112 | 112 | 112 |

[1]TPABr is tetrapropylammonium bromide.
[2]The pH meter was calibratd with a standard buffer solution at a pH of 10.0.
[3]The crystallizer leaked during the first night of crystallization and the subsequent loss of ammonia may have caused the lack of crystallization.

EXAMPLE XVI

Five additional samples of borosilicates were prepared. However, in these preparations, relatively high concentrations of ammonium hydroxide were employed.

For each of the preparations in this example, the quantities of chemicals employed are presented hereinafter in Table XIX. For each preparation, boric acid and tetrapropylammonium bromide were dissolved in water in a 4-liter beaker. Ammonium hydroxide solution (28%–30% ammonium hydroxide) was added to the solution, which was vigorously stirred for two minutes after the addition. Ludox AS-40 was added to the solution and the stirring was continued for three minutes. The pH of the resulting mixture was obtained and is the value shown hereinbelow in Table XIX. Then the mixture was placed in a 3-liter autoclave and heated at a temperature of 165° C. (329° F.) for the specified number of days. The product was removed from the autoclave on the day following the specified day, and was handled according to the method described in Examples X through XII, except that the drying temperature was 110° C. (230° F.). In each case, the material was identified by X-ray diffraction patterns as being AMS-1B crystalline borosilicate material. In view of these experiments, we have found no upper limit for the ammonium hydroxide concentration that is employed in the preparation of the AMS-1B crystalline borosilicates of the present invention.

TABLE XIX

PREPARATION INFORMATION - PREPARATIONS AT HIGH AMMONIUM HYDROXIDE CONCENTRATIONS

| REACTANT | PREPARATION NO. | | | | |
|---|---|---|---|---|---|
|  | 28 | 29 | 30 | 31 | 32 |
| DIST. WATER, gm | 1,300 | 1,400 | 900 | 600 | 900 |
| $H_3BO_3$, gm | 50 | 53 | 50 | 34 | 10 |
| TPABr[1], gm | 250 | 250 | 250 | 250 | 250 |
| CONC. $NH_4OH$, gm | 920 | 800 | 1,325 | 883 | 1,360 |
| LUDOX, AS-40, gm | 290 | 290 | 290 | 210 | 290 |
| pH | 11.17 | 11.14 | 11.27 | 11.42 | 11.85 |
| CRYSTALLINITY, % | 100 | 100 | 100 | 100 | 100 |
| DAYS AT 165° C. | 5 | 7 | 5[2] | 5 | 5 |

[1]TPABr is tetrapropylammonium bromide.
[2]All liquid and evaporated during digestion.

What is claimed is:

1. A method for preparing a metal-cationdeficient borosilicate, which method comprises: (1) preparing a mixture containing an oxide of silicon which is substantially free of metal cations, an oxide of boron, ammonium hydroxide, alkylammonium cation or a precursor of an alkylammonium cation, and water; and (2) maintaining said mixture at suitable reaction conditions to effect formation of said borosilicate, said reaction conditions comprising a reaction temperature within the range of about 25° C. (77° F.) to about 300° C. (572° F.), a pressure of at least the vapor pressure of water at the reaction temperature, and a reaction time that is sufficient to effect crystallization.

2. The method of claim 1, wherein said reaction conditions include a pH of the slurry prior to crystallization that falls within the range of about 8.2 to about 11.5.

3. The method of claim 1, wherein said reaction time is within the range of about 8 hours to about 3 weeks.

4. The method of claim 1, wherein the composition of said mixture falls within the following ranges of mole ratios of initial reactants:
$SiO_2/B_2O_3$ 1–400
$R_2O/[R_2O+(NH_4)_2O]$ 0.01–1
$NH_4+/[NH_4++M^n]$ 0.7–1
$NH_3/SiO_2$ 0.02–20
$H_2O/NH_3$ 2–2,000
wherein R is an alkylamine or an alkylammonium cation, and M is at least one metal cation having a valence of n.

5. The method of claim 2, wherein said reaction time is within the range of about 8 hours to about 3 weeks.

6. The method of claim 2, wherein the composition of said mixture falls within the following ranges of mole ratios of initial reactants:
$SiO_2/B_2O_3$ 1–400
$R_2O/[R_2O+(NH_4)_2O]$ 0.01–1
$NH_4+/[NH_4++M^n]$ 0.7–1
$NH_3/SiO_2$ 0.02–20
$H_2O/NH_3$ 2–2,000
wherein R is an alkylamine or an alkylammonium cation, and M is at least one metal cation having a valence of n.

7. The method of claim 5, wherein the composition of said mixture falls within the following ranges of mole ratios of initial reactants:
$SiO_2/B_2O_3$ 1–400
$R_2O/[R_2O+(NH_4)_2O]$ 0.01–1
$NH_4+/[NH_4++M^n]$ 0.7–1
$NH_3/SiO_2$ 0.02–20
$H_2O/NH_3$ 2–2,000
wherein R is an alkylamine or an alkylammonium cation, and M is at least one metal cation having a valence of n.

8. The method of claim 5, wherein the composition of said mixture falls within the following ranges of mole ratios of initial reactants:
$SiO_2/B_2O_3$ 2–150
$R_2O/[R_2O+(NH_4)_2O]$ 0.01–1
$NH_4+/[NH_4++M^n]$ 0.9–1
$NH_3/SiO_2$ 0.02–8
$H_2O/NH_3$ 5–2,000
wherein R is an alkylamine or an alkylammonium cation, and M is at least one metal cation having a valence of n.

9. The method of claim 5, wherein said reaction temperature is within the range of about 90° C. (194° F.) to about 225° C. (437° F.), said pH is within the range of about 8.4 to about 11.2, said reaction time is within the range of about 1 day to about 12 days, and the composition of said mixture falls within the following ranges of mole ratios of initial reactants:
$SiO_2/B_2O_3$ 1–400
$R_2O/[R_2O+(NH_4)_2O]$ 0.01–1
$NH_4+/[NH_4++M^n]$ 0.7–1
$NH_3/SiO_2$ 0.02–20
$H_2O/NH_3$ 2–2,000
wherein R is an alkylamine or an alkylammonium cation, and M is at least one metal cation having a valence of n.

10. The method of claim 9, wherein the composition of said mixture falls within the following ranges of mole ratios of initial reactants:
$SiO_2/B_2O_3$ 2–150
$R_2O/[R_2O+(NH_4)_2O]$ 0.01–1
$NH_4+/[NH_4++M^n]$ 0.9–1
$NH_3/SiO_2$ 0.02–8
$H_2O/NH_3$ 5–2,000
wherein R is an alkylamine or an alkylammonium cation, and M is at least one metal cation having a valence of n.

* * * * *